United States Patent [19]

Carpentier

[11] Patent Number: 4,605,408
[45] Date of Patent: * Aug. 12, 1986

[54] ARTIFICIAL CARDIAC VALVE WITH ACTIVE OPENING

[75] Inventor: Alain Carpentier, Paris, France

[73] Assignee: Universite Pierre et Marie Curie Paris VI, France

[*] Notice: The portion of the term of this patent subsequent to Jul. 3, 1996 has been disclaimed.

[21] Appl. No.: 594,736

[22] Filed: Mar. 29, 1984

[30] Foreign Application Priority Data

Mar. 30, 1983 [FR] France ............... 83 05274

[51] Int. Cl.[4] ............................................. A61F 2/24
[52] U.S. Cl. ............................................. 623/2; 251/65
[58] Field of Search ......................... 3/1, 1.5; 251/65

[56] References Cited

U.S. PATENT DOCUMENTS

| | | | |
|---|---|---|---|
| 3,039,481 | 6/1962 | Schreiber et al. | 251/65 X |
| 3,370,305 | 2/1968 | Goott et al. | 3/1 |
| 3,859,668 | 1/1975 | Anderson | 3/1 |
| 3,974,854 | 8/1976 | Kurpanek | 137/512 |
| 4,159,543 | 7/1979 | Carpentier | 3/1.5 |
| 4,417,360 | 11/1983 | Moasser | 251/65 X |

Primary Examiner—Richard J. Apley
Assistant Examiner—Alan W. Cannon
Attorney, Agent, or Firm—Bacon & Thomas

[57] ABSTRACT

The present invention relates to a cardiac valve comprising a seat and at least one mobile element ensuring opening and closure of the valve, characterized in that said seat and/or said mobile element comprises at least one device, known per se, which ensures controlled opening of said valve when the blood pressure is balanced on both sides of said mobile element.

4 Claims, 6 Drawing Figures

ARTIFICIAL CARDIAC VALVE WITH ACTIVE OPENING

The present invention relates to an artificial cardiac valve adapted to be implanted in humans.

It is known to replace human cardiac valves by prostheses which all present a check valve device allowing the blood to flow in one direction and preventing it from flowing back in the other. These valves comprise either a plastic ball playing in a cage (Starr-Edwards valve) and alternately clearing and obstructing a metal seat fixed to the heart, a disc moving parallel in a cage according to the same modalities as above (Beall valve), or an oscillating disc held by two claws (Björk valve).

These prostheses risk provoking coagulation of the blood, which may block the mechanism of the prosthesis and/or produce embolisms. This risk is principally associated with the very configuration of these prostheses which produce turbulences around the ball or the disc occluding the valve.

Another mechanism, called "butterfly valve", constituted by an elastomer disc fixed to a central spindle (Gott) is also known. This disc rests during closure time on radially disposed spicules implanted on the valve body. By reason of the existence of a fixed central spindle and of spicules creating turbulences, the risks of coagulation are also considerable and this prosthesis has been abandoned.

French Patent Application No. 75 36074 (published under No. 2 331 997) discloses an artificial valve comprising:

(a) a substantially circular ring comprising suture means of type known per se, (b) two mobile, semi-circular check valves resting on an inner ramp of this ring, (c) a hinge system with double displacement allowing said check valves to make movements of rotation then of translation clearing the hinge system, which device, by the "washing" that it occasions, makes it possible to reduce the risks of coagulation.

Whatever the qualities of the various artificial valves known at present, they present two major drawbacks:

(1) These are valves with passive opening, opening solely under mechanical stresses (pressure gradients) and not valves with active opening, which open by themselves like the natural, so-called mitral valves, at the appropriate time in the absence of any pressure gradient, thus allowing better filling of the ventricles;

(2) these valves are noisy, producing during closure time a metallic sound which is audible both to the patient and to any one in the vicinity.

It is an object of the present invention to overcome the difficulties mentioned hereinabove for the various artificial valves and to provide, for the first time, a valve with active opening, i.e. a valve which, when the blood pressures on either side of the valve are identical, is slightly open.

This valve with active opening further enables a haemodynamic yield to be obtained which is about 25% greater than the yield of the valves available at present and consequently makes it possible to reduce the risks of coagulation of the blood and to improve the cardiac work. Finally, wear of the valve will be improved.

The cardiac valve with active opening according to the invention is composed of a seat (or fixing ring) and at least one mobile element (check valve) and is characterised in that at least said seat or said check valve comprises a device, known per se, which ensures controlled opening of the valve when it is at rest, i.e. when the blood pressure on both sides of the valve is balanced.

Said known device may be of mechanical or magnetic type, this not being limiting. In the mechanical devices, a spring blade fixed on the seat will, for example, be used, which will ensure a certain thrust which, at balance, will therefore provoke a certain opening of the valve. In the magnetic systems, there will be at least one small permanent magnet on the edge of a check valve and at least one small permanent magnet in the seat, for example, these two magnets being so positioned as to exert a controlled repellant effect one on the other.

The device ensuring controlled opening of the valve when the latter is at rest may be used more particularly in the valves described in French Pat. No. 75 36074. Moreover, said valves may include the following substantial improvements over what is described in said Patent.

These improvements which may be implemented individually or in combination are as follows:

In Pat. No. 74 36074, the check valves pivot about two parallel axes constituted by two cylindrical rods (parallel, fast with the ring); it may be desirable to replace these two material spindles by two protuberances each fixed on the ring and together forming a fictitious axis positioned in the same way as the parallel cylindrical rods of the previous design.

In Pat. No. 75 36074, the outer face of the check valve is provided with barbs which surround the cylindrical rod forming axis and guide the displacement of the check valve in translation; it may be desirable to avoid the presence of these barbs and to arrange the upper face of the check valve so that this face presents, in that part thereof which will be in contact with the material spindle or the protuberances according to the invention, a swell forming a groove in which said material spindle or said protuberances are inserted for said check valve to pivot.

The invention will be more readily understood on reading the following description with reference to the accompanying drawings, in which.

Figure 1:
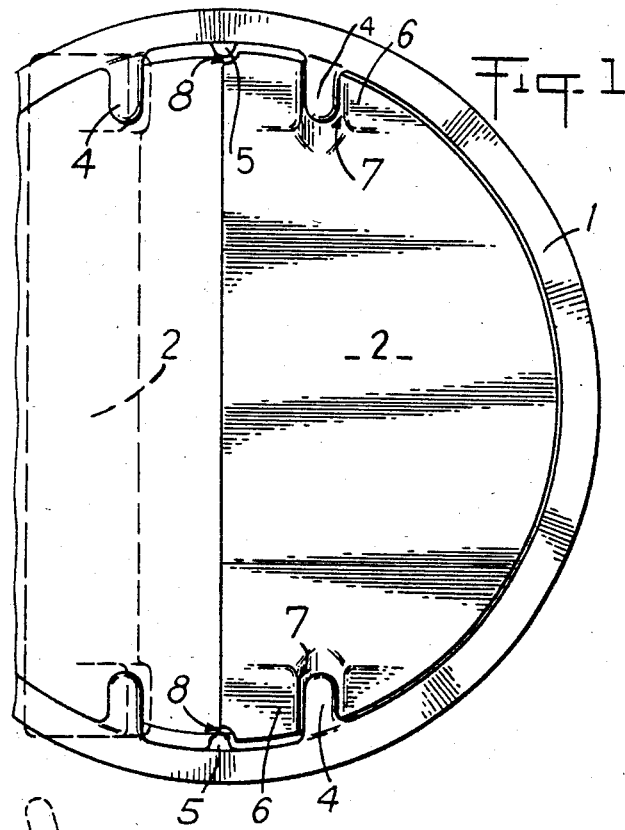
FIG. 1 is a plan view of one of the symmetrical halves of the circular cardiac valve.

Referring now to the drawings, the cardiac valve according to the invention essentially comprises two parts: a fixed part 1 and at least one mobile part 2.

The fixed part 1 is composed of a circular ring for example made of metal or pyrolytic carbon whose inner face presents a swell 3 on which the edges of the check valve or valves abut to close the cardiac valve. Said swell 3 is suitably interrupted to allow the check valves to pivot. This fixed part also comprises suitably disposed protuberances 4; these protuberances (two for each check valve) constitute the axis about which the check valve will pivot. Finally, the fixed part further presents two diametrically opposite swells 5 which constitute a stop rail to limit rearward displacement of the check valves and on which rail the rear part of the check valves abuts during rotation of said valves.

The mobile part 2 is constituted by two generally flat, thin, semi-circular check valves which are preferably made of pyrolitic carbon or plastics material.

Figure 3:
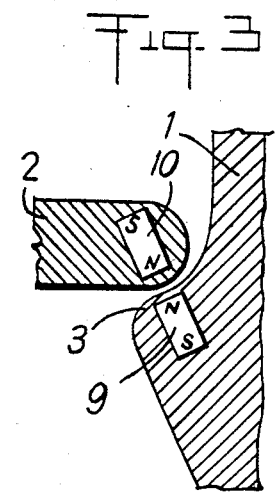
FIG. 3 shows a magnetic device for active opening.
Figure 4A:
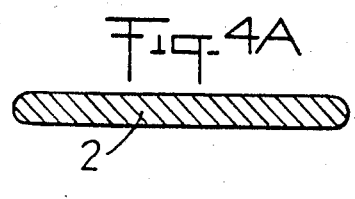
FIGS. 4A and 4B show a transverse section through a check valve at two levels (central section 4A and on the edge, at the level of the swell of the check valve, section 4B).
Figure 2:
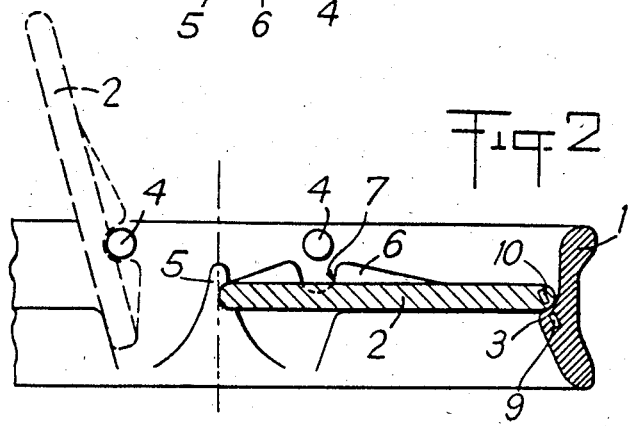
FIG. 2 is a view in section through a diametrical plane of the prosthesis, this view also showing a symmetrical half of the prosthesis.
Figure 4B:
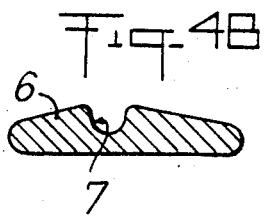

The upper face of each check valve presents, at the spot where the check valve will be in contact with the protuberances 4, two swells 6 of which each comprises a groove 7. During opening of the check valve, each protuberance 4 is inserted in said groove 7 in order subsequently to ensure pivoting of the check valve about the axis formed by the protuberances 4—4. During closure of the check valve, the circulating blood will ensure washing of the hinge zone constituted by the protuberances 4 and the groove 7. The check valves comprise a notch 8 at the ends of their linear part which corresponds to the stop rail 5, thus controlling the displacement of the check valves in translation and in rotation. The cardiac valve as described hereinabove comprises the improvements made to the cardiac valves described in French Pat. No. 75 36074. However, according to the invention, said cardiac valve must also comprise at least one device which ensures active opening therefor. The device shown in FIG. 3 is constituted by two magnets disposed opposite each other, the poles of the same sign facing each other, one of these magnets 9 being fast with the ring 1 forming the fixed part of the cardiac valve and the other magnet 10 being fast with the check valve 2 of the cardiac valve; in FIG. 3, these two magnets are embedded in each of the parts constituting the cardiac valve. There may, of course, be several pairs of magnets over the periphery of the cardiac valve.

Magnets 9 and/or 10 may be housed in a suitable excess thickness of the fixed part and of the mobile check valve; they may also be glued on the surface of these two pieces or finely disposed (case of microscopic or ultramicroscopic magnets) in the material which constitutes the fixed part and/or the mobile part of the cardiac valve.

The various magnets disposed on the periphery of the check valve may be replaced by a single magnet which is semi-circular in shape or whose general form is that of a portion of circle.

It is also possible to replace the permanent magnets by electromagnets; in particular, the combination may be used of a light magnetic piece located in the mobile part (check valve) of the cardiac valve with an electromagnet disposed in the fixed part of the valve.

Figure 5:
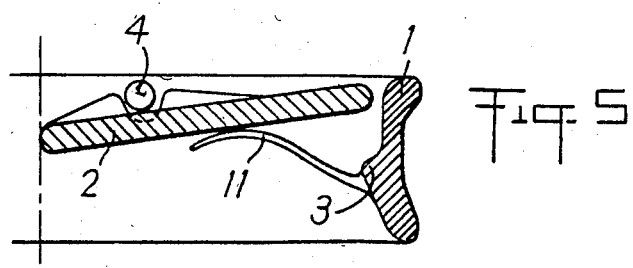
FIG. 5 shows a mechanical device for active opening, in partial section.

The device shown in FIG. 5 is constituted essentially by a spring 11 made of a resilient metal, which is fixed to the fixed part of the cardiac valve and which, at rest, maintains the check valve in slightly open position.

What is claimed is:

1. A cardiac valve comprising a fixed seat having a passage for blood flow therethrough including a circular ring comprising suture means and a swell, a mobile check unit for opening and closing the passage including two substantially semi-circular check valves, each check valve including two swells and whose edges rest on the swell on said ring when the valve is closed, said check valves effecting in their displacements a movement of translation and a movement of rotation, wherein the axes of rotation of each valve are constituted by two protuberances each fixed on the ring and together forming a common axis, said protuberances cooperating with grooves made in the two swells of each check valve, and means for maintaining the check unit in a controlled opened position when blood pressure is balanced on both sides thereof.

2. A cardiac valve comprising a fixed seat having a passage for blood flow therethrough including a circular ring comprising suture means and a swell, a mobile check unit for opening and closing the passage including two substantially semi-circular check valves, each check valve including two swells and whose edges rest on the swell on said ring when the valve is closed, said check valves effecting in their displacements a movement of translation and a movement of rotation, wherein the axes of rotation of each valve are constituted by two protuberances each fixed on the ring and together forming a common axis, said protuberances cooperating with grooves made in the two swells of each check valve, and means for maintaining the check unit in a controlled opened position when blood pressure is balanced on both sides thereof including a pair of magnets, with one magnet being carried by the check unit and the other magnet being carried by the fixed seat, wherein the magnets are disposed with the poles of the same polarity facing opposite each other.

3. A cardiac valve comprising a fixed seat having a passage for blood flow therethrough including a circular ring comprising suture means and a swell, a mobile check unit for opening and closing the passage including two substantially semi-circular check valves, each check valve including two swells and whose edges rest on the swell on said ring when the valve is closed, said check valves effecting in their displacements a movement of translation and a movement of rotation, wherein the axes of rotation of each valve are constituted by two protuberances each fixed on the ring and together forming a common axis, said protuberances cooperating with grooves made in the two swells of each check valve, and means for maintaining the check unit in a controlled opened position when blood pressure is balanced on both sides thereof including a spring carried by the fixed seat for engagement by the check unit.

4. The valve of claim 1, 2 or 3 wherein the ring comprises on its inner face two stop rails which control the displacement of the check valves in translation and in rotation.

* * * * *